ns Patent [19]

United States Patent [19]

Marion et al.

[11] 4,115,434
[45] Sep. 19, 1978

[54] CATALYSTS AND PROCESSES FOR PREPARING UNSATURATED NITRILES

[75] Inventors: Jacques Marion; Christian Pralus, both of Lyons, France

[73] Assignee: Produits Chimiques Ugine Kuhlmann, Paris, France

[21] Appl. No.: 789,869

[22] Filed: Apr. 22, 1977

[51] Int. Cl.² .................. B01J 23/84; C07C 120/02
[52] U.S. Cl. .................................. 260/465.3; 252/469
[58] Field of Search .......................... 252/456, 469; 260/465.3

[56] References Cited

U.S. PATENT DOCUMENTS

| | | | |
|---|---|---|---|
| 3,625,867 | 12/1971 | Yoshino et al. | 260/465.3 |
| 3,769,241 | 10/1973 | Stewart et al. | 252/469 |
| 3,914,278 | 10/1975 | Gasson et al. | 260/465.3 |
| 4,000,177 | 12/1976 | Marion et al. | 252/456 |
| 4,009,194 | 2/1977 | Umemura et al. | 252/456 |
| 4,035,410 | 7/1977 | Marion et al. | 260/465.3 |
| 4,040,983 | 8/1977 | Innes et al. | 260/465.3 |

Primary Examiner—O. R. Vertiz
Assistant Examiner—Wayne A. Langel
Attorney, Agent, or Firm—Brooks, Haidt, Haffner & Delahunty

[57] ABSTRACT

Catalysts for the preparation of unsaturated nitriles by the ammoxidation of olefins, the catalysts comprising a combination of the oxides of antimony, tin, zirconium, copper, and tungsten having the general formula:

$$Sb_a Sn_b Zr_c Cu_d W_e O_f$$

where $a$ is from 1 to 10, $b$ is from 1 to 10, $c$ is 1, $d$ is from 0.01 to 5, $e$ is from 0.01 to 0.05, and $f$ is the number of oxygen atoms in the oxidized combination with the metallic elements, together with processes for the preparation of nitriles by olefin ammoxidation, particularly acrylonitrile produced by ammoxidizing propylene, using such catalysts.

14 Claims, No Drawings

CATALYSTS AND PROCESSES FOR PREPARING UNSATURATED NITRILES

BACKGROUND OF THE INVENTION

The present invention relates to the preparation of unsaturated nitriles starting with olefins, and more particularly, it relates to the vapor phase ammoxidation of propylene or isobutene, respectively, to acrylonitrile or methacrylonitrile in the presence of catalysts based on antimony and tin.

THE INVENTION

It has been unexpectedly found that the catalytic properties of compositions prepared by the addition of various polyvalent metal oxides to oxides of antimony and tin in certain formulas is particularly useful for carrying out the ammoxidation of olefins to unsaturated nitriles. Particularly, a combination of the oxides of antimony, tin, zirconium, copper, and tungsten is useful for the ammoxidation of propylene to acrylonitrile.

The catalysts of the present invention can be represented by the following empirical formula:

$$Sb_1 Sn_b Zr_c Cu_d W_e O_f \qquad (I)$$

in which $a$ is from about 1 to 10, $b$ is from about 1 to 10, $c$ is 1, $d$ is from 0.01 to 5, $e$ is from about 0.01 to 0.05, and $f$ is the number of oxygen atoms in the oxidized composition which is obtained by combination of the metallic elements of Formula (I). The particular value of $f$ depends upon the particular compositions obtained with the several elements, and is generally from about 5 to about 55.

The catalysts according to the present invention can be prepared in numerous ways, for example by intimate mixture of the oxides, by separate precipitation or coprecipitation starting from salts or soluble compounds of the constituent elements, by separate or simultaneous thermal decomposition of compounds convertible to oxides upon heating, or by a combination of these various techniques.

Whichever route is adopted for preparing the catalyst, it must undergo a thermal treatment at temperatures from 500° to 1000° C before use. This treatment is carried out under an oxygen-containing atmosphere, such as air, and it is preferred in certain embodiments to utilize a temperature of 700° to 900° C.

In one method for the preparation of the catalyst according to the present invention, antimony trioxide is disperesed in an aqueous nitric acid solution, and powdered metallic tin is added to the suspension of antimony trioxide with heating and agitation to convert the tin to its oxide. The remaining nitric acid is removed by succesive steps of decantation, siphoning and washing with cold and hot water.

Copper in the form of cupric nitrate, and tungsten and zirconium in the form of oxides $WO_3$ and $ZrO_2$, respectively, are added to the mixture of antimony and tin oxides suspended in water. The copper is precipitated in the form of its hydroxide by the addition of ammonia, and the precipitate is separated by filtration after decantation and washing with water. The precipitate is dried and converted into the desired form, for example, by pelleting, before thermal treatment in an air current.

Certain of the ingredients can be added after the drying or the calcination. In one preferred method, the catalyst is prepared by introducing tungsten in the form of ammonium paratungstate, dissolved in a minimum amount of water, to the mixture obtained after the previous operation of filtration and already containing antimony, tin, copper, and zirconium. The resulting mixture is dried and formed into the desired configuration as described previously. The catalyst according to the present invention so prepared has been shown to be particularly useful for catalysis of the ammoxidation reactions of olefins, particularly of propylene, under the conditions usually employed. In the case of propylene ammoxidation, the reactants used are oxygen, ammonia, and propylene. The propylene can optionally be mixed with paraffinic hydrocarbons such as those usually present in commercial propylene, that is, ethane and propane, among others.

As the oxygen source, air is usually used for reasons of cost. The molar ratios of oxygen/proplyene and ammonia/propylene can vary through a wide range of values. The molar ratio of oxygen to propylene is generally from 0.5 to 3, and in certain preferred embodiments is above 1.5. The molar ratio of ammonia/propylene is generally from about 0.7 to 3, and in certain preferred embodiments is from 0.9 to 1.5.

The catalytic conversion reaction of propylene to acrylonitrile is generally carried out in the presence of water vapor or an inert diluent which can comprise from 5 to 40% by volume of the total volume of reactants. In certain embodiments, the water vapor or inert diluent is from 10 to 25% by volume.

The reaction temperature is generally from 350° to 520° C, and is most frequently between 380° and 500° C. The reaction pressure can range from less than to greater than atmospheric pressure, and is desirably approximately atmospheric.

The contact time can vary over a large interval, for example, from about 0.5 to 10 seconds, and in preferred embodiments is generally between 1 and 6 seconds. Particularly preferred results are obtained for contact times of from 2 to 4 seconds which correspond to the demands of commercial usage.

The catalyst can be used in the form of pellets, cylinders, granules, or fine particles according to the type of reactor in which the catalyst is to be used, and in particular, according to whether it will be used in a fixed bed or a fluidized bed. The catalyst can be utilized either solely as a mixture of the oxides so prepared, or it can be used in an appropriate fashion according to known processes on a catayst support of the usual type, such as silica.

The following examples are given to illustrate embodiments of the invention as it is presently preferred to practice it. It will be understood that these examples are illustrative, and the invention is not to be considered as restricted thereto except as indicated in the appended claims.

In the following examples, the rate of conversion of olefins indicated is expressed as the number of moles of olefin converted to the given product per 100 moles of olefin fed.

EXAMPLE I

A catalyst according to the present invention is prepared by heating 2000 g of an aqueous nitric acid solution containing 18.5% by weight of $HNO_3$ with agitation to 95° C, whereupon 218.6 g of antimony oxide powder, $Sb_2O_3$, is dispersed in the solution. Then, 59.4 g of powdered tin is added while the temperature is kept at 97-99° C.

The suspension is then maintained at the boil for 15 minutes, and thereafter, always under agitation, cooled to 40° C. The agitation is then discontinued and after settling the supernatant liquid is removed by siphoning. The remaining paste is then washed under agitation for 15 minutes, first with 4 liters of cold water and then, after settling and removal of the supernatant liquid, anew with 4 liters of water at 98–100° C.

After cooling to 40° C, settling, and siphoning of the supernatant liquid, the paste is re-suspended in 2.5 liters of water and brought to 60° C, whereupon 43.5 g of cupric nitrate, $Cu(NO_3)_2 \cdot 3H_2O$, and 61.6 g of zirconium oxide, $ZrO_2$, are added. Ammonia is added until the pH reaches 6.3–6.5. After cooling, settling, and removal of the supernatant liquid, the solids are washed under agitation with 4 liters of cold water for 10 minutes and then separated from the liquid by filtration.

The solids are then charged to a mixer equipped with a heating jacket, and 2.02 g of ammonium paratungstate, $(NH_4)_6 W_7 O_{24} \cdot 6 H_2O$, previously dissolved in 200 ml of water, is added. An intimate mixture of ingredients is effected by mixing at the same time as the water is evaporated. The drying of the powder thus finally obtained is achieved by heating at 135° C for 12 hours. The catalyst is then pelleted after addition of 1 percent by weight of graphite to act as a lubricant.

The product so obtained is then thermally treated by heating at 800° C for 16 hours under an air stream.

The catalyst contains the metallic elements in the ratio Sb/Sn/Zr/Cu/W of 3/1/1/0.375/0.015, and 60 g thereof in the form of cylindrical pellets 5 by 4 mm is charged to a catalytic reactor comprised by a 10 mm I.D. glass U-tube. This tube is immersed in a molten nitrate bath heated to 460° C. A gaseous mixture having the following molar composition is passed through the catalyst at the rate of 18 L/hr:

Propylene ($C_3H_6$) 6%
Ammonia ($NH_3$) 7%
Air 70%
Water 17%

Under these conditions 77.4% of the propylene is converted to acrylonitrile, 6.1% to hydrogen cyanide, 0.8% to acrolein, 7.0% to $CO_2$, and 3.6% to carbon monoxide, 5.1% of the propylene not being converted.

EXAMPLE II

Sixty grams of a catalyst according to the invention in which the elements have the atomic ratio Sb/Sn/Zr/Cu/W of 3/1/1/0.25/0.015 and which is thermally treated at 800° C is tested in the same apparatus as Example I but at 470° C.

A gaseous feed mixture with the following molar composition is fed at the rate of 18 L/hr:

Propylene 7%
Ammonia 8%
Air 70%
Water 15%

Under these conditions, 79% of the propylene is converted to acrylonitrile, 0.6% to acrolein, 5.9% to hydrogen cyanide, 6.6% to carbon dioxide, and 3.2% to carbon monoxide, while 4.8% of the propylene is not converted.

EXAMPLE III

Seventy-five grams of a catalyst according to this invention wherein the atomic ratio of elements Sb/Sn/Zr/Cu/W is 3/1/1/0.375/0.015 thermally treated at 820° C. is tested in a 14 mm I.D. catalytic reactor with a 21.6 L/hr gaseous feed mixture with the molar constitution:

Propylene 6.5%
Ammonia 7.5%
Air 68.0%
Water 18.0%

In this test, 77.8% of the propylene is converted to acrylonitrile, 1.2% to acrolein, 5.8% to hydrogen cyanide, 7.9% to carbon dioxide, and 3.2% to carbon monoxide, 4.1% of the propylene not being converted.

EXAMPLE IV

Seventy-five grams of the catalyst of Example III in the form of 3 to 5 mm granules is tested at 460° C. in the same equipment used in Example III, using a flow rate of 21.6 L/hr of a gaseous mixture having the same composition as in Example I.

Under these conditions 80.7% of the propylene is converted to acrylonitrile, 0.5% to acrolein, 5.7% to hydrogen cyanide, 7.3% to carbon dioxide, and 3.2% to carbon monoxide, only 2.6% of the propylene not being converted.

What is claimed is:

1. A catalyst for the production of unsaturated nitriles by ammoxidation of olefins, the catalyst consisting essentially of a combination of the oxides of antimony, tin, zirconium, copper, and tungsten according to the formula:

$$Sb_a Sn_b Zr_c Cu_d W_e O_f$$

where $a$ is from 1 to 10, $b$ is from 1 to 10, $c$ is 1, $d$ is from 0.01 to 5, $e$ is from 0.01 to 0.05, and $f$ is the number of oxygen atoms in combination with the oxygenated compounds.

2. A catalyst according to claim 1 which is heat-treated at a temperature of 700° C. to 900° C.

3. A catalyst according to claim 1 wherein $f$ is from 5 to 55.

4. A catalyst according to claim 1 which is heat-treated at a temperature of from 500° C. to 1000° C.

5. A catalyst according to claim 4 wherein the heat treatment is carried out in an oxygen-containing atmosphere.

6. A process for the ammoxidation of olefins to produce the corresponding nitriles, which process comprises contacting a gaseous mixture of the olefin, an oxygen-containing gas, and ammonia with the catalyst of claim 1 to convert the olefin to the nitrile, and recovering the nitrile so produced.

7. A process according to claim 6 wherein the temperature is from 350° C. to 520° C.

8. A process according to claim 6 wherein the temperature is from 380° C. to 500° C.

9. A process according to claim 6 wherein the pressure is substantially atmospheric.

10. A process according to claim 6 wherein the contact time is from about 0.5 to about 10 seconds.

11. A process according to claim 6 wherein the contact time is from 4 to 6 seconds.

12. A process according to claim 6 wherein the olefin is propylene or isobutene.

13. A process according to claim 6 wherein an inert diluent is additionally present.

14. A process according to claim 13 wherein the inert diluent is nitrogen, water vapor, or a mixture thereof.

* * * * *

UNITED STATES PATENT AND TRADEMARK OFFICE
CERTIFICATE OF CORRECTION

PATENT NO. : 4,115,434
DATED : September 19, 1978
INVENTOR(S) : JACQUES MARION ET AL It is certified that error appears in the above-identified patent and that said Letters Patent are hereby corrected as shown below:

Title page, insert --[30] Foreign Application Priority Data
Jun. 4, 1976  France  76 16926 --

Column 1, line 25, change "$Sb_1$" to --$Sb_a$--; line 50, correct the spelling of "dispersed"; line 54, correct the spelling of "successive".

Column 2, line 17, correct the spelling of "propylene".

Column 3, line 43, correct the spelling of "acrolein"; line 47, change "inventionin" to --invention in--.

Signed and Sealed this

Twenty-ninth Day of May 1979

[SEAL]

Attest:

RUTH C. MASON
Attesting Officer

DONALD W. BANNER
Commissioner of Patents and Trademarks